United States Patent [19]

Ebner

[11] 4,405,498
[45] Sep. 20, 1983

[54] OXIDATION AND AMMOXIDATION CATALYSTS

[75] Inventor: Jerry R. Ebner, St. Charles, Mo.

[73] Assignee: Monsanto Company, St. Louis, Mo.

[21] Appl. No.: 254,231

[22] Filed: Apr. 14, 1981

Related U.S. Application Data

[63] Continuation-in-part of Ser. No. 104,625, Dec. 17, 1979, abandoned.

[51] Int. Cl.³ .................. B01J 21/02; B01J 27/14; B01J 27/02; B01J 29/16
[52] U.S. Cl. .................. 252/432; 252/435; 252/437; 252/439; 252/456; 252/464; 252/467
[58] Field of Search .............. 252/432, 435, 437, 439, 252/456, 464, 467

[56] References Cited

U.S. PATENT DOCUMENTS

| | | | |
|---|---|---|---|
| 3,681,421 | 8/1972 | Barclay et al. | 260/465.3 |
| 3,773,692 | 11/1973 | Hensel et al. | 252/456 X |
| 3,879,453 | 4/1975 | Ono et al. | 252/456 X |
| 4,035,418 | 7/1977 | Okada et al. | 252/439 X |
| 4,040,978 | 8/1977 | Li | 252/456 X |
| 4,062,885 | 12/1977 | Mekhtiev et al. | 252/467 X |
| 4,065,468 | 12/1977 | Grasselli et al. | 252/432 X |
| 4,093,558 | 6/1978 | Grasselli et al. | 252/464 X |
| 4,138,366 | 2/1979 | Shaw et al. | 252/467 X |
| 4,148,757 | 4/1979 | Brazdil et al. | 252/432 |
| 4,180,678 | 12/1979 | Wada et al. | 252/435 X |
| 4,212,766 | 7/1980 | Brazdil et al. | 252/432 |
| 4,309,361 | 1/1982 | Suresh et al. | 252/432 |

FOREIGN PATENT DOCUMENTS 43-23926 7/1968 Japan .................. 252/464

Primary Examiner—Delbert E. Gantz
Assistant Examiner—William G. Wright
Attorney, Agent, or Firm—Richard D. Stone; Roger R. Jones; P. L. Passley

[57] ABSTRACT

Disclosed herein are catalysts useful for oxidation and ammoxidation of hydrocarbons. Such catalysts have the empirical formula

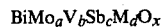

$BiMo_aV_bSb_cM_dO_x$ wherein a is 0.5–2, b is 0.12–3, c is 0.12–10, d is 0–0.5 and x is selected to satisfy the valence requirements of the other elements present. In such catalysts, M is one or more elements selected from Groups I-A, II-A, III-A, V-A, VI-A, I-B, IV-B, VI-B and VII-B of the Periodic Table.

Catalysts according to the invention are prepared by forming a slurry of vanadium antimonate component, a bismuth molybdate component, and optionally the compound M and/or a support material, drying the slurry, and calcining to form the catalyst.

Such catalysts are specifically useful for production of acrylonitrile from propylene, ammonia and an oxygen-containing gas.

17 Claims, No Drawings

OXIDATION AND AMMOXIDATION CATALYSTS

BACKGROUND OF THE INVENTION

This is a continuation-in-part of copending Application Ser. No. 104,625 filed Dec. 17, 1979 now abandoned.

This invention relates to oxidation and/or ammoxidation catalysts containing the elements, bismuth, molybdenum, antimony, vanadium and oxygen, and optionally containing one or more additional metal elements and to a method of preparing such catalysts. In another aspect, this invention relates to a process employing such catalysts.

It is well known that olefins can be oxidized to oxygenated hydrocarbons such as unsaturated aldehydes and acids, for example, acrolein and methacrolein, and acrylic and methacrylic acid. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

Many catalysts are disclosed as suitable in the foregoing reactions. One such catalyst is described in Example 3 of U.S. Pat. No. 3,681,421. This catalyst employs oxides of antimony, vanadium, and at least one additional polyvalent metal which may be titanium in the proportion of 1 gram of antimony, 0.12–0.5 gram atoms of vanadium, and 0.25–0.5 gram atoms of titanium. Under the conditions of that example, a yield of 56% of acrylonitrile was obtained using propylene, ammonia, air and steam as reactants.

Further, U.S. Pat. No. 4,062,885 discloses the preparation of phthalonitrile by ammoxidation of orthoxylene in the presence of a supported catalyst of the general formula $Bi_aSb_bMo_cV_dO_x$ wherein $a=1-20$, $b=1-10$, $c=0.1-15$ and $d=1-20$. Use of such a catalyst for oxidation or ammoxidation reactions involving unsaturated aliphatic hydrocarbons is not mentioned, however.

More recently, U.S. Pat. No. 4,093,558 discloses oxidation catalysts, composed of the oxides of antimony, molybdenum, at least one of iron and vanadium, and optionally an additional element which may be bismuth. These catalysts are useful for manufacture of maleic anhydride from butane.

Preparation of ammoxidation catalysts by preforming bismuth molybdate and then mixing the preformed bismuth molybdate with other elements is disclosed in U.S. Pat. No. 4,040,978.

It is well known that the economics of acrylonitrile manufacture dictate increasingly higher yields and selectivity of conversion of the reactants to acrylonitrile in order to minimize the difficulties attending purification of the product and handling of large recycle streams. Moreover, it is known that prior art catalysts frequently produce relatively large quantities of undesired oxygen-containing by-products such as $CO_2$, acrolein and/or acrylic acid which must be removed in purification of the acrylonitrile.

SUMMARY OF THE INVENTION

It is an object of this invention to provide a novel catalyst composition useful in the preparation of unsaturated aliphatic nitriles by ammoxidation of aliphatic olefins.

Yet another object is to provide a catalyst which is useful for oxidation of aliphatic olefins to the corresponding unsaturated aldehyde.

A more specific object of this invention is to provide a catalyst which gives surprisingly higher yields and selectivity of conversion of propylene, ammonia and air to acrylonitrile than do prior art catalysts.

It is a further object to provide a catalyst which minimizes the production of oxygenated by-products of acrylonitrile, such as $CO_2$, acrolein, acrylic acid and the like.

Still another object is to provide a catalyst which exhibits substantially its full activity immediately upon startup of an ammoxidation process, i.e., which requires no break-in period under ammoxidation conditions in order to exhibit its full efficiency in terms of activity and selectivity.

A further object of this invention is to provide a process for manufacture of such a catalyst.

In another aspect, it is an object of this invention to provide an ammoxidation process which employs such a catalyst.

To achieve these and other objects which will become apparent, a catalyst is provided having the empirical formula $BiMo_aV_bSb_cM_dO_x$ wherein $a=0.5-2$, $b=0.12-3$, $c=0.12-10$, $d=0-0.5$ and x is chosen to satisfy the valence requirements of the other elements present and in which M is one or more elements selected from Groups I-A, II-A, III-A, V-A, VI-A, I-B, IV-B, and VII-B of the Periodic Table of the Elements. According to the present invention, such a catalyst is prepared by forming a slurry containing preformed vanadium antimonate, a bismuth molybdate component and optionally one or more elements, and drying and calcining the resultant mixture.

As used herein, the term "bismuth molybdate" means a chemical compound of bismuth, molybdenum and oxygen. Such compounds may be formed by the interaction of bismuth and molybdenum oxides which have been dry mixed and calcined, or by precipitation preferably from an aqueous solution, for example. The "bismuth molybdate" component of catalysts according to this invention may contain oxides of bismuth and/or molybdenum, in addition to bismuth molybdate compounds.

Likewise, as used herein the term "vanadium antimonate" is employed to designate complex mixtures of vanadium, antimony and oxygen. Compounds which may be formed by the interaction of antimony compounds and vanadium compounds are intended to be included within the term "vanadium antimonate" as used herein. The "vanadium antimonate" component of these catalysts may contain free oxides of antimony and/or vanadium.

The vanadium antimonate component may be a compound which is formed under conditions of calcination in air at elevated temperatures; however, as used herein, the term vanadium antimonate also includes precursors of true vanadium antimonate compounds. Such precursors are prepared, for example, by preparing an aqueous slurry of a vandium compound and an antimony compound. The slurry is boiled until the contained solids turn greenish-brown, indicating the partial interaction or a vanadium antimonate compound, the nature of which is not fully understood. The vanadium antimonate precursor may, if desired, be calcined to form a true vanadium antimonate compound as will be more fully explained hereinafter.

The bismuth molybdate component of catalysts according to this invention is preferably prepared by forming an aqueous solution of a bismuth salt, forming an aqueous solution of a molybdenum-containing salt, oxide, or hydroxide, combining these two solutions, and recovering the precipitated bismuth molybdate by filtration or decantation. Suitable bismuth compounds include, but are not limited to bismuth metal when used as a solution with nitric acid, bismuth oxide, bismuth trinitrate pentahydrate and bismuth halides when hydrolyzed. Similarly, suitable molybdenum compounds include molybdenum trioxide, molybdic acid, ammonium molybdates, such as ammonium dimolybdate and ammonium heptamolybdate and molybdenum halides.

The bismuth molybdate components of catalysts according to this invention is preferably prepared in the absence of the vanadium antimonate component. However, the bismuth molybdate component may, if desired, be prepared in the presence of preformed vanadium antimonate.

It is known that bismuth molybdate may exist in alpha, beta and gamma forms or phases. An interesting and informative source of information on these forms of bismuth molybdate is found in *Journal of Solid State Chemistry*, Vol. 13, pp. 228–297 (1975), authored by Tu Chen and G. S. Smith. The alpha bismuth molybdate has the molecular formula $Bi_2(MoO_4)_3$, while the beta form is $Bi_2Mo_2O_9$ and the gamma form has the formula $Bi_2MoO_6$. Particularly preferred catalysts according to this invention employ predominantly the beta bismuth molybdate phase with lesser amounts of the alpha phase present.

The vanadium antimonate component of these catalysts may be formed by adding a vanadium-containing compound to an aqueous slurry of an antimony-containing compound and boiling the resultant slurry. In a preferred preparation, the vanadium and antimony compounds are the oxides $V_2O_5$ and $Sb_2O_3$. The slurry is boiled until the contained solids turn greenish-brown, indicating the interaction or partial reaction of the two metal oxides to form a precursor of vanadium antimonate. In a still more preferred preparation procedure, a vanadyl oxalate solution is prepared by adding oxalic acid slowly to an aqueous slurry of ammonium metavanadate at about 60° C. until evolution of $CO_2$ ceases. To the clear blue solution of vanadyl oxalate is added the desired amount of antimony trioxide and the resulting slurry is dried to form the vanadium antimonate precursor. In any case, a particularly preferred embodiment of this invention, the greenish-brown vanadium antimonate precursor is dried and calcined for ½ to 24 hours at a temperature of 500° to 800° C., preferably 550° to 750° C. to form a grayish-black vanadium antimonate compound.

Although it is preferred to use the oxides of vanadium and antimony as described above in preparing the vanadium antimonate component of the catalyst, other antimony and vanadium-containing compounds may be employed. Exemplary of such antimony compounds are antimony trioxide, antimony tetroxide, antimony pentoxide and antimonic acid. Compounds which form an oxide of antimony after chemical reaction or calcination are also suitable. For example, metallic antimony, antimony hydroxides and antimony halides, such as antimony trichloride, tribromide and antimony pentachloride. Suitable vanadium compounds include vanadium oxides, such as vanadium pentoxide, tetroxide or trioxide, vanadium oxalate, ammonium metavanadate and vanadium halides. The vanadyl oxalate is preferably prepared in situ by reaction of the vanadium compound with oxalic acid, such as $V_2O_5$, $HVO_3$ or $NH_4VO_3$.

Following preparation of the bismuth molybdate and vanadium antimonate components to the catalyst, these components are combined in the desired proportions and well mixed, preferably in an aqueous slurry. At this point, a suitable catalyst support and/or one or more additional metal components may be added, if desired, as described below.

The aqueous slurry, if a slurry is employed, is then heated to remove the bulk of the aqueous phase. The concentrated slurry contains a certain amount of water and it is desirable to remove this water by some form of drying process to form a dry catalyst precursor. This can take the form of a simple oven-drying process in which the water containing solid phase is subjected to a temperature that is sufficiently high to vaporize the water and completely dry the solid phase.

An alternate drying process which may be employed is the so-called spray-drying process in which water-containing solid phase particles are sprayed into contact with hot gas (usually air) so as to vaporize the water. The drying is controlled by the temperature of the gas and the distance the particles travel in contact with the gas. It is generally undesirable to adjust these parameters to achieve too rapid drying as this results in a tendency to form dried skins on the partially dried particles of the solid phase which are subsequently ruptured as water occluded within the particles vaporizes and attempts to escape. By the same token, it is desirable to provide the catalyst in a form having as little occluded water as possible. Therefore, where a fluidized bed reactor is to be used and microspheroidal particles are desired, it is advisable to choose the conditions of spray-drying with a view of achieving substantially complete drying without particle rupture.

Following the drying operation, the catalyst precursor is calcined to form the catalyst. The calcination process is usually conducted in air at essentially atmospheric pressure and at a temperature of about 500° C. to about 800° C., such as from about 525° C. to about 650° C. The time to complete the calcination can be anything up to 10 hours, but for most purposes, the calcination need take only from about 1 to 2 hours.

In some applications, it may be advantageous to include in the catalyst a support material which may or may not be active catalytically but which functions by providing a large surface area for the catalyst and by creating a harder and more durable catalyst for use in the highly abrasive environment of a fluidized bed reactor. This support material can be any of those commonly proposed for such use such as, for example, silica, zirconia, alumina, titania, antimony pentoxide sol or other oxide substrates. From the point of view of availability, cost and performance, silica is usually a satisfactory support material and is preferably in the form of silica sol for easy dispersion.

The proportions in which the components of the supported catalyst are present can vary widely but it is usually preferred that the support provides from 10 to 90% and most preferably about 35 to 60% by weight of the total combined weight of the catalyst and the support. To incorporate a support into the catalyst, the support material is preferably added to the slurry containing the active components discussed above.

As has been stated, catalysts according to this invention are those having the empirical formula $BiMo_aV_bSb_cM_dO_x$, where a is from 0.5-2, b is from 0.12-3, c is from 0.12-10, d is from 0-0.5 and x is taken to satisfy the valence requirements of the other elements present. In more preferred embodiments of such catalysts, a is from 0.7-1.5, b is from 0.12-1, c is from 0.12-3 and d is from 0-0.2.

In many instances, it may be desirable to modify the catalyst physical properties or the spectrum of by-products made in, for example, ammoxidation processes in which these catalysts are employed. Further, it may be desirable to modify the physical properties of the catalyst somewhat. To this end, one or more additional elements may be incorporated into the catalyst formulation. Depending upon the particular property sought to be modified, suitable additive elements may include one or more elements selected from Groups I-A, II-A, III-A, V-A, VI-A, I-B, IV-B, VI-B and VII-B of the Periodic Table of elements. Compound or compounds of the desired element(s) are conveniently added to the mixture containing the active bismuth molybdate and vanadium antimonate components, either before or after addition of the silica sol or other support material, if a support material is employed.

Specifically preferred among the modifying additive elements are potassium, calcium, magnesium, boron, thallium, arsenic, phosphorus, selenium, tellurium, silver, titanium, zirconium, tungsten and manganese, and antimony although other modifier elements may be employed.

The catalyst preparation of the invention yields a catalyst that is particularly useful in the production of acrylonitrile from propylene and in which follows specific reference is made to that process although it should be understood that the described catalyst is also useful for ammoxidation of other olefins and for oxidation of aliphatic olefins to aldehydes and acids.

In the most frequently used ammoxidation processes, a mixture of olefin, ammonia and oxygen (or air) is fed into a reactor and through a bed of catalyst particles. The reaction temperature is usually in the range of 400° C. to 550° C. and preferably 450° C. to 525° C., and the pressure is 1 to 6 atmospheres (100 to 600 kPa). The ammonia and olefin are required stoichiometrically in equimolar amounts, but it is usually necessary to operate with a molar ratio of ammonia to olefin in excess of 1 to reduce the incidence of side reactions. Likewise, the stoichiometric oxygen requirement is 1.5 times the molar amount of olefin. The feed mixture is commonly introduced into the catalyst bed at a W/F (defined as the weight of the catalyst in grams divided by the flow of reactant stream in ml/sec. at standard temperature and pressure) in the range of 2 to about 15, preferably from about 4 to about 10.

The ammoxidation reaction is exothermic and for convenience in heat distribution and removal the catalyst bed is desirably fluidized; however, fixed catalyst beds may be employed with alternative heat removal means such as cooling coils within the bed.

The catalyst prepared by the process of the present invention is particularly well adapted for use in such a process and in which follows its effectiveness and advantages over prior art catalysts are demonstrated in the context of that process.

SPECIFIC EMBODIMENTS

As has been stated above, the catalyst of the invention has the empirical formula $BiMo_aV_bSb_cM_dO_x$, wherein a=0.5-2, b=0.12-3, c=0.12=10, d=0-0.5 and x is a number taken to satisfy the valence requirements of the other elements present in the catalyst, optionally dispersed on a finely divided support which represents from 10 to 90% of the supported catalyst weight. In the examples that are presented below, specific compositions within this range were prepared and employed as catalysts in the ammoxidation of propylene to produce acrylonitrile.

As used in the following examples, the following terms are defined in the following manner:

1. "W/F" is defined as the weight of the catalyst in grams divided by the flow rate of reactant stream in ml/sec. measured at S.T.P.

2. "Propylene ($C_3H_6$) conversion" is defined as:

$$\frac{\text{Mols } C_3H_6 \text{ in feed} - \text{mols } C_3H_6 \text{ in effluent}}{\text{Mols } C_3H_6 \text{ in feed}} \times 100\%$$

3. "Acrylonitrile (AN) selectivity" is defined as:

$$\frac{\text{Mols } AN \text{ in effluent}}{\text{Mols } C_3H_6 \text{ converted}} \times 100\%$$

4. "Acrylonitrile (AN) yield" is defined as:

$$\frac{\text{Mols } AN \text{ formed}}{\text{Mols } C_3H_6 \text{ feed}} \times 100\%$$

In the following examples, unless otherwise noted, the catalysts of the examples were evaluated to determine acrylonitrile selectivity and yield and propylene conversion in a fluidized bed reaction vessel having an inside diameter of about 12.8 millimeters. Approximately 25 grams of catalyst was used in each case. A reactant mixture of 17-17.8 volume % $O_2$, 7.6-8.3 volume % propylene ($C_3H_6$), 8-9% volume % $NH_3$, and the balance helium was passed upward through the catalyst bed at a rate sufficient to give the value of W/F shown in the experimental results for each example. The temperatures shown in the examples are expressed in degrees Celsius, and in each instance the pressure at which the reaction was carried out was 207 kPa unless otherwise noted.

EXAMPLE 1

A catalyst according to the present invention was prepared by the following technique.

Bismuth Molybdate Component 28.78 grams of molybdenum oxide ($MoO_3$) were dissolved in a mixture of 72 ml of water and 36 ml of concentrated ammonium hydroxide, added to a solution of 97 grams of bismuth nitrate pentahydrate in ~184 ml of water and 30 ml of concentrated nitric acid with stirring, and the pH of the resulting mixture was adjusted to between 3 and 6.5 using ammonium hydroxide whereafter it was boiled for approximately 3 hours. The precipitate was filtered and washed with approximately 1000 ml of water.

Vanadium Antimonate Component

To an aqueous slurry of 10.20 grams of antimony trioxide ($Sb_2O_3$) in ~20 ml of water was added 3.18 grams of vanadium pentoxide ($V_2O_5$). The mixture was stirred and boiled until the mixture turns greenish-brown in color and becomes a paste. This is the vanadium antimonate precursor. It was dried 12–16 hours at 150°–200° C. and then calcined for 2–3 hours at 750° C. to give grayish-black vanadium antimonate.

Catalyst

To 223 grams of a silica sol containing 40% silica and adjusted to a pH of ~2.0 with concentrated nitric acid were added with vigorous stirring the bismuth molybdate and vanadium antimonate components. The pH was maintained from 2 to 4. The catalyst mixture was milled to obtain a homogeneous dispersion of ingredients. Portions of the mixture were tray dried and other portions were spray dried. Each was then calcined in air at 550° C. for 1 hour to obtain a catalyst having catalytic elements in the following atomic proportions: $Bi_1Mo_1V_{0.175}Sb_{0.35}O_x$ supported on 50% by weight silica.

These catalysts were charged into the reaction vessel described above and the following results were obtained:

| Temperature | W/F | % AN Yield | % AN Selectivity | % $C_3H_6$ Conversion |
|---|---|---|---|---|
| 475 | 3 | 70 | 77 | 90 (tray dried) |
| 475 | 5 | 72 | 75 | 96 (tray dried) |
| 475 | 4.8 | 75 | 77 | 98 (spray dried) |

EXAMPLE 2

To demonstrate the effect of using as the vanadium antimonate component the vanadium antimonate precursor (as defined above), a catalyst having the composition of the catalyst of Example 1 was prepared as follows:

Vanadium Antimonate Component

To an aqueous slurry of 10.20 grams of $Sb_2O_3$ antimony trioxide in ~20 ml of water was added 3.18 grams of ($V_2O_5$) vanadium pentoxide. The mixture was stirred and boiled until the mixture turns greenish-brown in color and becomes a paste. This is the vanadium antimonate precursor.

Catalyst

To 223 grams of a silica sol containing 40% silica and adjusted to a pH of ~2.0 with concentrated nitric acid were added with vigorous stirring the bismuth molybdate and vanadium antimonate. The pH was maintained from 2 to 4. The mixture was tray dried or spray dried and calcined 1 hour at 545° C. to 555° C. to give a composition having the essential catalytic elements in the following atomic proportions $Bi_1Mo_1V_{0.175}Sb_{0.35}O_x$ supported on 50% by weight silica.

When evaluated in the reactor vessel used in Example 1, this catalyst gave the following results:

| Temperature | W/F | % AN Yield | % AN Selectivity | % $C_3H_6$ Conversion |
|---|---|---|---|---|
| 475 | 3 | 70 | 77 | 91 |
| 475 | 5 | 70 | 74 | 96 |

EXAMPLE 3

To show the importance of forming a vanadium antimonate or precursor thereof prior to addition of the bismuth molybdate to the slurry, a catalyst having the empirical formula of the catalysts of Examples 1 and 2 was prepared as follows:

Catalyst

To 223 grams of a silica sol containing 40% silica and adjusted to a pH of ~2.0 with concentrated nitric acid were added with vigorous stirring 10.20 grams of antimony trioxide, the bismuth molybdate and then 3.18 grams of vanadium pentoxide. The pH is maintained from 2 to 4. The mixture was boiled down to a paste, tray dried and calcined 1 hour at 545° C. to 555° C. to give a composition having the essential catalytic elements in the following proportions $Bi_1Mo_1V_{0.175}Sb_{0.35}O_x$ supported on 50% by weight silica.

The catalyst was evaluated as in the preceding examples with the following results:

| Temperature | W/F | % AN Yield | % AN Selectivity | % $C_3H_6$ Conversion |
|---|---|---|---|---|
| 475 | 3 | 59 | 72 | 83 |
| 475 | 5 | 63 | 69 | 92 |

From these results, it can be seen that the acrylonitrile yield is increased by about 10% when a catalyst according to the present invention is employed, as compared to a catalyst which is made without a vanadium antimonate or a precursor thereof.

EXAMPLES 4–10

To show the effect of varying ratios of vanadium antimonate component to bismuth molybdate, catalysts having the empirical formulae shown in the following Table were prepared. In each instance, the catalysts were prepared by forming a bismuth molybdate precipitate and a calcined vanadium antimonate component as in Example 1. These components were mixed in varying ratios, slurried with silica sol, dried, and calcined as in Example 1 to give catalysts containing the percentages of silica and having active catalytic oxide components with the empirical formulae shown in the Table below.

TABLE

| Example | Empirical Formula | % $SiO_2$ | Temp. | W/F | % AN Yield | % AN Selectivity |
|---|---|---|---|---|---|---|
| 4 | $BiMo_1V_{.025}Sb_{.05}O_x$ | 40 | 450 | 4.0 | 67* | 71* |
| 5 | $BiMo_1V_{.10}Sb_{.20}O_x$ | 50 | 475 | 4.0 | 71 | 75 |
| 6 | $BiMo_1V_{.25}Sb_{.5}O_x$ | 38 | 475 | 4.2 | 73 | 76 |
| 7 | $BiMo_{1.11}V_{.3}Sb_{.6}O_x$ | 50 | 475 | 4.0 | 70 | 74 |
| 8 | $BiMo_1V_{.625}Sb_{1.25}O_x$ | 37 | 470 | 4.6 | 71 | 76 |
| 9 | $BiMo_1V_{.75}Sb_{1.5}O_x$ | 38 | 455 | 3.1 | 59 | 69 |
| 10 | $BiMo_1V_1Sb_2O_x$ | 38 | 451 | 5.3 | 57 | 68 |

*Pressure was 122 kPa in Example 4

EXAMPLES 11-16

To show the effect of varying the ratio of bismuth to molybdenum and the ratio of vanadium to antimony in catalysts according to the present invention, the following examples were performed. In each example that follows, the procedure of Example 1 was followed with the exception that the ratios of the components were varied to obtain catalysts having the empirical formulae shown in the following Table.

EXAMPLE 17

To show a particularly preferred embodiment of the present invention, a catalyst was prepared in which the vanadium antimonate component was made using vanadyl oxalate as the source of vanadium as follows.

Bismuth Molybdate Preparation 86.36 grams of molybdenum oxide ($MoO_3$) were dissolved in a mixture of 205 ml of water and 108 ml of concentrated ammonium hydroxide and added to a solution of 125.81 grams of bismuth oxide ($Bi_2O_3$) in 170 ml of concentrated nitric acid (70% $HNO_3$) and 370 ml of water with stirring. The pH of the resulting mixture was adjusted to 6.5 with $NH_4OH$ whereafter it was held at 65° C. for approximately 3 hours. The precipitate was filtered and washed with approximately one liter of water.

Vanadium Antimonate Preparation 40.0 grams of $Sb_2O_3$ were added to a vanadyl oxalate solution prepared by adding 35 grams of oxalic acid ($H_2C_2O_4.2H_2O$) to a warm (~55° C.) aqueous mixture of 16.04 grams of ammonium metavanadate ($NH_4VO_3$) in 35 ml of water. The reaction mixture was dried at 110° C. and the vanadium antimonate precursor so obtained was calcined in an air flow at 550° C. for 2 hours.

TABLE

| Example | Empirical Formula | Temp. | W/F | % AN Yield | % AN Selectivity |
|---|---|---|---|---|---|
| 11 | $BiMo_{.5}V_{.175}Sb_{.35}O_x$ | 475 | 5.0 | 45 | 62 |
| 12 | $BiMo_1V_{.33}Sb_1O_x$ | 465 | 4.4 | 62 | 70 |
| 13 | $BiMo_1V_{.175}Sb_{.4375}O_x$ | 475 | 4.5 | 71 | 75 |
| 14 | $BiMo_1V_{.175}Sb_{.219}O_x$ | 470 | 5.0 | 71 | 75 |
| 15 | $BiMo_1V_{.175}Sb_{.175}O_x$ | 475 | 5.0 | 69 | 71 |
| 16 | $BiMo_1V_{.175}Sb_{.308}O_x$ | 475 | 5.0 | 69 | 75 |

Catalyst Preparation

The vanadium antimonate (54.62 grams) was added to 400 gms of 40% silica sol and the mixture was milled overnight. To the milled mixture was added 224.3 grams of silica sol (40%), sufficient $HNO_3$ to bring the pH to about 1, and the bismuth molybdate. The catalyst mixture was homogenized while maintaining the pH from 2 to 3 with $HNO_3$, spray dried, and calcined 1 hour at 550° C. to give a composition having the essential catalytic elements in the following atomic proportions: $Bi Mo_{1.11}V_{0.253}Sb_{0.51}O_x$ supported on 50% by weight silica.

The catalyst so prepared was evaluated in a reactor as in Example 1 at 475° C., 207 kPa pressure and a value of W/F of 5. The observed AN yield was 72% and the AN selectivity was 75%.

EXAMPLES 18-31

To illustrate the effect of addition of one or more additional elements to catalysts according to this invention, the following Examples were performed:

Preparation of Bismuth Molybdate 340 grams of $Bi(NO_3)_3.5H_2O$ was added to a solution of 200 mls of concentrated (70%) $HNO_3$ dissolved in 950 mls of $H_2O$ and the resulting solution was stirred and heated to 60° C. To the bismuth nitrate solution an ammonium molybdate solution was added slowly with stirring. The ammonium molybdate was prepared by dissolving 100 gms of $MoO_3$ in a solution of 150 mls of 58% $NH_4OH$ and 1000 mls of $H_2O$. The pH of the bismuth molybdate slurry was adjusted to 3.5 by addition of 58% $NH_4OH$ and was then heated and stirred for about 20 hours at 65° C. The resulting bismuth molybdate was filtered and washed with distilled water.

Preparation of Vanadium Antimonate

A slurry of antimony trioxide ($Sb_2O_3$) and water was prepared by mixing 165.5 gms of $Sb_2O_3$ with 150 mls of $H_2O$. 51.5 gms of ground $V_2O_5$ was added to the antimony trioxide and the resulting slurry was stirred and heated until it turned into a greenish-brown paste. The paste was then placed in a flat pan and dried overnight at 130° C. This solid was ground to a fine powder and calcined at 750° C. for 2 hours, after which it was ground with a mortar and pestle to less than 50 microns particle size.

Preparation of Catalysts 73 grams of Nalco #2327 40% silica sol was placed in a blender and the pH was adjusted to 3.7 with 70% $HNO_3$. 110.3 gms of bismuth molybdate component (0.10 moles of Bi and Mo prepared as above) was added to the silica sol. To this mixture was added 10 gms vanadium antimonate component prepared as above and the mixture was reslurried. To the slurry was added 1.6 gms of $TiO_2$. To a second slurry thus prepared was added 2.46 gms of $ZrO_2$ and to a third such slurry was added 7 ml of 0.1 molar solution of $KNO_3$. After addition of the promoters the slurries were heated and stirred until they became a thick paste. Each paste was then placed in a flat pan and dried overnight at 130° C. and then calcined at 550° C. for one hour.

Other catalysts containing one of the following elements: P, B, Ca, Tl, Ag, Mn, W were prepared in a similar manner using respectively the following compounds as additive sources: $H_3PO_4$, $H_3BO_3$, $Ca(NO_3)_2$, $TlNO_3$, $AgNO_3$, $Mn(CH_3CO_2)_2$ and $H_2WO_4$, respectively. A final catalyst was similarly prepared having two additional elements, K and B, added to the catalyst slurry as $K_2B_4O_7.4H_2O$.

All catalysts were tested in reactor system using a reactant feed of artificial air (He+$O_2$), ammonia and propylene in the ratios: (10.6-9.99:1.1-1.05:1.0) and operated at a W/F of 3, a temperature of 475° C. and a pressure of 205 kPa. The results are shown in the following table.

The catalysts made by the foregoing procedure had the empirical formula of catalytic elements as shown in the table. The percent silica in the final catalyst in each instance is also shown in the table.

TABLE

| EXAMPLE | EMPIRICAL FORMULA | % SILICA | W/F | % AN YIELD | % AN SELECTIVITY |
|---|---|---|---|---|---|
| 18 | $BiMo_1V_{.25}Sb_{.5}Ti_{.2}O_x$ | 38 | 3.6 | 68 | 72 |
| 19 | $BiMo_1V_{.25}Sb_{.5}Zr_{.2}O_x$ | 38 | 4.5 | 70 | 74 |
| 20 | $BiMo_1V_{.25}Sb_{.5}K_{.14}O_x$ | 50 | 3 | 64 | 71 |
| 21 | $BiMo_{1.1}V_{.175}Sb_{.35}P_{.1}O_x$ | 50 | 3 | 64 | 71 |
| 22 | $BiMo_{1.1}V_{.175}Sb_{.35}B_{.1}O_x$ | 50 | 3 | 65 | 72 |
| 23 | $BiMo_{1.1}V_{.175}Sb_{.35}Ca_{.1}O_x$ | 50 | 3 | 68 | 73 |
| 24 | $BiMo_{1.1}V_{.175}Sb_{.35}K_{.1}O_x$ | 50 | 3 | 66 | 77 |
| 25 | $BiMo_{1.1}V_{.175}Sb_{.35}Tl_{.1}O_x$ | 50 | 3 | 70 | 73 |
| 26 | $BiMo_{1.1}V_{.175}Sb_{.35}Ag_{.1}O_x$ | 50 | 3 | 66 | 74 |
| 27 | $BiMo_{1.1}V_{.175}Sb_{.35}Mn_{.1}O_x$ | 50 | 3 | 62 | 69 |
| 28 | $BiMo_{1.1}V_{.175}Sb_{.35}W_{.1}O_x$ | 50 | 3 | 69 | 73 |
| 29 | $BiMo_{1.1}V_{.175}Sb_{.35}K_{.05}B_{.1}O_x$ | 50 | 3 | 49 | 69 |
| 30 | $BiMo_{1.1}V_{.175}Sb_{.35}K_{.01}B_{.02}O_x$ | 50 | 3 | 66 | 74 |
| 31 | $BiMo_{1.1}V_{.175}Sb_{.35}B_1O_x$ | 50 | 3 | 68 | 73 |

EXAMPLE 32

To illustrate a catalyst in which the catalyst or promoter element M of a catalyst having the empirical formula $BiMo_aV_bSb_cM_dO_x$ is additional antimony added to the slurry of bismuth molybdate component and preformed vanadium antimonate component, the following experiment was preformed.

Bismuth Molybdate Component 86.36 grams of molybdenum oxide ($MoO_3$) were dissolved in a mixture of 205 ml of water and 108 ml of concentrated ammonium hydroxide, added to a solution of 125.81 grams of bismuth oxide ($Bi_2O_3$) in 170 ml of concentrated nitric acid (70% $HNO_3$) and 370 ml of water with stirring, and the pH of the resulting mixture was adjusted to 6.5 with $NH_4OH$, whereafter it was held at 65° C. for approximately 3 hours. The precipitate was filtered and washed with approximately one liter of water.

Vanadium Antimonate Component 27.58 grams of $Sb_2O_3$ were added to a vanadyl oxalate solution prepared by adding 24 grams of oxalic acid ($H_2C_2O_4.2H_2O$) to a warm (~55° C.) aqueous mixture of 11.06 grams of ammonium metavanadate ($NH_4VO_3$) in 25 ml of water. The reaction mixture was dried at 110° C. and the vanadium antimonate precursor so obtained was calcined in an air flow at 550° C. for 2 hours.

Catalyst Preparation

The vanadium antimonate and 19.67 grams of $Sb_2O_3$ were added to 400 gms of 40% AS silica sol, and the mixture was milled overnight. To the milled mixture were added 273 grams of silica sol (40%), sufficient $HNO_3$ to bring the pH to about 1, and the bismuth molybdate. The catalyst mixture was homogenized while maintaining the pH from 2 to 3 with $NHO_3$, spray dried, and calcined 1 hour at 550° C. to give a composition having the essential catalytic elements in the following atomic proportions $BiMO_{1.11}V_{0.175}Sb_{0.35}Sb_{0.25}O_x$ supported on 50% by weight silica.

The catalyst above was evaluated in an ammoxidation reactor system as in the case of previous catalysts, and the following results were obtained at a reaction pressure of 205 kPa and temperature of 475° C.

| W/F | % AN Yield | % AN Selectivity |
|---|---|---|
| 3 | 74 | 77 |
| 5 | 74 | 76 |

I claim:

1. A catalyst for oxidation and ammoxidation of hydrocarbons comprising catalytic elements having the empirical formula

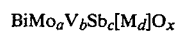

$BiMo_aV_bSb_c[M_d]O_x$ wherein a is from 0.5 to 2, b is from 0.12 to 3, c is from 0.12 to 10, and x is taken to satisfy the valence requirements of the other elements present said catalyst being prepared by forming a mixture containing a preformed vanadium antimonate component and a bismuth molybdate component forming said mixture into dry particles, and calcining at a temperature of from 500° to 850° C.

2. A catalyst according to claim 1 wherein said catalyst contains $M_d$, wherein d is from 0 to 0.5 and M is one or more elements selected from Groups I-A, II-A, III-A, V-A, VI-A, I-B, IV-B, VI-B, and VII-B of the Periodic Table, and said catalyst is prepared by forming a mixture containing a preformed vanadium antimonate component, a bismuth molybdate component, and a compound of M, forming said mixture into dry particles, and calcining at a temperature of from 500° to 850° C.

3. A catalyst according to claim 2 wherein M is one or more elements selected from potassium, calcium, manganese, boron, thallium, arsenic, phosphorus, selenium, tellurium, silver, titanium, zirconium, tungsten, manganese and antimony.

4. A catalyst according to claim 2 wherein a is from 0.7 to 1.5, b is from 0.12 to 1, c is from 0.12 to 3 and d is from 0 to 0.5.

5. A catalyst according to claim 2 wherein said mixture is an aqueous slurry.

6. A catalyst according to claim 4 wherein said vanadium antimonate component and said bismuth molybdate component are separately formed prior to forming said slurry.

7. A catalyst according to claim 5 wherein said vanadium antimonate component is calcined prior to forming said slurry.

8. A catalyst according to claim 5 wherein said vanadium antimonate component is preformed and said bismuth molybdate component is formed in the presence of said preformed vanadium antimonate.

9. A catalyst according to claim 8 wherein said vanadium antimonate component is calcined prior to forming said slurry.

10. A catalyst according to claim 4 wherein said mixture is an aqueous slurry.

11. A catalyst according to claim 10 wherein said vanadium antimonate component and said bismuth molybdate component are separately preformed prior to forming said slurry.

12. A catalyst according to claim 11 wherein said vanadium antimonate component is calcined prior to forming said slurry.

13. A catalyst according to claim 12 wherein a support material comprising from about 10 to about 90% of the total weight of said catalyst is added to said slurry.

14. A catalyst according to claim 13 wherein said support material comprises from about 35 to about 60% of the total weight of said catalyst.

15. A catalyst according to claim 14 wherein said support material is silica.

16. A catalyst according to claim 11 wherein said vanadium antimonate component is formed by combination of an antimony compound with a solution containing vanadyl oxalate.

17. A catalyst according to claim 11 wherein M is antimony.

* * * * *